(12) United States Patent
Cao et al.

(10) Patent No.: US 8,354,649 B2
(45) Date of Patent: Jan. 15, 2013

(54) APPARATUS FOR THE EXTENSION AND RETRACTION OF A PERIPHERAL DEVICE

(75) Inventors: Yang Cao, Beijing (CN); Hongbin Zhao, Beijing (CN); Huiliang Wang, Beijing (CN); Duncan Bourne, Redhill (GB)

(73) Assignee: Elekta AB (publ), Stockholm (SE)

( * ) Notice: Subject to any disclaimer, the term of this patent is extended or adjusted under 35 U.S.C. 154(b) by 83 days.

(21) Appl. No.: 13/069,887

(22) Filed: Mar. 23, 2011

(65) Prior Publication Data
US 2012/0241638 A1 Sep. 27, 2012

(51) Int. Cl.
*H05G 1/02* (2006.01)
(52) U.S. Cl. ..................................................... 250/393
(58) Field of Classification Search ............... 250/393
See application file for complete search history.

(56) References Cited

U.S. PATENT DOCUMENTS

| | | | | |
|---|---|---|---|---|
| 4,216,381 A * | 8/1980 | Lange | ...................... | 250/363.05 |
| 4,774,412 A * | 9/1988 | Kurkake | .................. | 250/363.08 |
| 4,927,127 A * | 5/1990 | Lock | ................................ | 5/611 |
| 5,047,641 A * | 9/1991 | Besseling et al. | ........ | 250/363.08 |
| 5,670,783 A * | 9/1997 | Ray | .......................... | 250/363.05 |
| 6,519,316 B1 * | 2/2003 | Collins | .......................... | 378/65 |
| 8,061,678 B2 * | 11/2011 | Stefan | .......................... | 248/651 |
| 2007/0079443 A1 * | 4/2007 | Hoth et al. | ......................... | 5/601 |
| 2007/0158515 A1 * | 7/2007 | Dittmer et al. | ............. | 248/283.1 |
| 2009/0050763 A1 * | 2/2009 | Dittmer | ...................... | 248/284.1 |
| 2009/0304153 A1 * | 12/2009 | Amelia et al. | .................. | 378/65 |
| 2011/0170660 A1 * | 7/2011 | Atzinger et al. | ................ | 378/51 |

* cited by examiner

*Primary Examiner* — Marcus Taningco
(74) *Attorney, Agent, or Firm* — Sunstein Kann Murphy & Timbers LLP

(57) ABSTRACT

The present invention provides an extendible support mechanism in which a counterbalance system allows extension and retraction of the arm to be carried out with the same level of mechanical effort. Embodiments of the present invention allow the system to be used in a plurality of orientations, and thus the invention has particular utility in the extension and retraction of peripheral devices for radiotherapy systems, where use of a rotatable gantry is common.

10 Claims, 5 Drawing Sheets

APPARATUS FOR THE EXTENSION AND RETRACTION OF A PERIPHERAL DEVICE

FIELD OF THE INVENTION

The present invention relates to an extendible support apparatus, and particularly to an apparatus supporting an imaging device or other peripheral device in a radiotherapy system.

BACKGROUND

EPIDs (Electronic Portal Imaging Device) are widely used with linear accelerators (linacs) for patient setup verification and records. Such an imaging device sits opposite the linear accelerator, in line with the radiation beam, such that in use the patient is positioned between the two. The EPID therefore detects the (therapeutic) radiation after it has passed through the patient, and the image produced illustrates the extent of the radiation beam and its alignment with a treatment region (e.g., a tumour) within the patient.

It is common for the radiation beam to be rotated around the patient during a course of radiotherapy, allowing the therapeutic radiation to be directed towards the target region in the patient from a number of different directions. By keeping the target region at or close to the isocentre of the system, collateral damage to tissue surrounding the target can be minimized. To achieve this, both the radiation source and the EPID tend to be mounted on opposite sides of a rotatable gantry.

EPIDs are usually mounted on an extension arm to allow the device to be extended into the path of the radiation beam during use, and retracted when not in use. A conventional arrangement is shown in FIGS. 1a and 1b, with the former showing the apparatus in its extended form and the latter showing the apparatus in its retracted form.

The apparatus has a mount 12 for connection to the gantry of the radiotherapy system, a detector 16 which folds outwards to lie transverse to the radiation beam, and an extending arm 14 connecting the detector 16 to the mount 12.

The extension arm 14 has a "scissors" structure, i.e. two members are pivotally linked to one another at their centres to form a pair of members, and a plurality of such pairs are linked to each other by pivotal connection at their respective ends. By opening or closing one pair of interconnected members, each pair in the arm is also opened or closed, resulting in extension or retraction of the arm as a whole. It can also be seen that the detector 16 unfolds as the arm 14 extends, although this is not crucial.

The scissors structure presents some problems, however. For example, the connections of the mount 12 and the detector 16 to respective ends of the extending arm 14 are difficult. To simplify the connecting mechanism in each case, the end of one cross-member is positionally fixed to the mount/detector, and the other cross-member is slidably connected to the mount/detector (both are able to pivot). In this way, the arm 14 is reliably connected at each end. However, the act of extending or retracting the arm then results in a raising or lowering of the centre of gravity of the arm and the detector 16. For example, although FIGS. 1a and 1b are schematic, it can be seen that the centre of gravity in the latter arrangement is higher (i.e. up the page) than in the former arrangement.

This situation is further complicated by the rotation of the gantry. At some angles of rotation, gravity will act on the arm and detector so as to force the arm to retract; at other (opposite) angles of rotation, gravity will act in the opposite direction, forcing the arm to extend. In intermediate angles of rotation, the centre of gravity may move laterally or in a direction having both lateral and vertical components.

What is needed is an extension mechanism which works reliably and with the same level of effort regardless of the angle of rotation of the gantry.

SUMMARY OF THE INVENTION

According to one aspect of the present invention, there is provided an apparatus for supporting a device, comprising: a mount; a scissors-type extension arm comprising, at a first end, a first contact point positionally fixed but pivotally connected to the mount and a second contact point pivotally and slidably connected to the mount, and, at a second end, an interface for connection to the device; and a counterbalancing system, coupled to the second contact point, arranged to counterbalance the scissors-type extension arm and the device in a plurality of spatial orientations of the apparatus.

In an embodiment, the second contact point is slidable in two, opposing directions, corresponding to extension and retraction of the scissors type extension arm. The counterbalancing system is arranged to counterbalance movement of the second contact point in either direction.

The counterbalancing system may comprise a counterweight coupled to the second contact point of the scissors-type extension arm. To allow for counterbalancing in all angles of rotation of the apparatus, the counterweight may be coupled to the second contact point as from a plurality of directions (and particularly from the two slidable directions of the sliding contact point).

In a further aspect of the present invention, there is provided an imaging apparatus for a radiotherapy system, comprising: a mount, for fixing to the radiotherapy system; an imaging device; an arm coupling the imaging device to the mount, the arm and imaging device having a combined centre of gravity, the arm being capable of extension, resulting in movement of the centre of gravity in a first direction, and retraction, resulting in movement of the centre of gravity in a second, opposite direction; and a counterweight, coupled to the arm so as to move in a direction opposing the movement of the centre of gravity when the arm is extended or retracted.

In a yet further aspect of the present invention, there is provided a radiotherapy apparatus, comprising: a rotatable gantry; a source of radiation, mounted on the gantry; a peripheral device, mounted on the gantry via an extension arm comprising a first contact point positionally fixed but pivotally connected to the gantry and a second contact point pivotally and slidably connected to the gantry; and a counterbalancing system, coupled to the second contact point, arranged to counterbalance the extension arm and the peripheral device at a plurality of angles of rotation of the gantry.

The peripheral device may be any apparatus, but in one embodiment is an imaging apparatus, wherein the source of radiation and the imaging apparatus are mounted on substantially opposite sides of the gantry, that is, where the axis of rotation of the gantry lies between the source of radiation and the imaging apparatus.

In a still further aspect of the present invention, there is provided a peripheral apparatus for a radiotherapy system, comprising: a mount, for fixing to the radiotherapy system; a peripheral device; an arm coupling the peripheral device to the mount, the arm and peripheral device having a combined centre of gravity, the arm being capable of extension, resulting in movement of the centre of gravity in a first direction, and retraction, resulting in movement of the centre of gravity in a second, opposite direction; and a counterweight, coupled to the arm so as to move in a direction opposing the movement of the centre of gravity when the arm is extended or retracted.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1B:
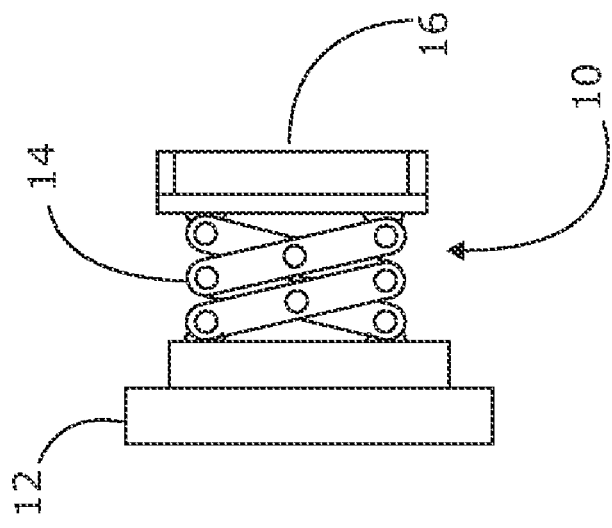
FIGS. 1a and 1b show schematically a conventional extension arm and imaging apparatus in its extended position and its retracted position, respectively.
Figure 1A:
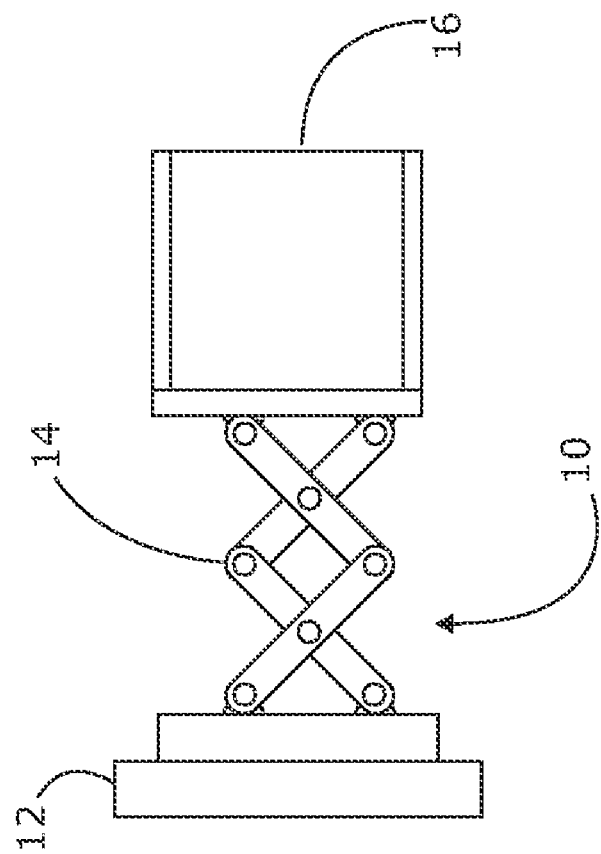
Figure 2:
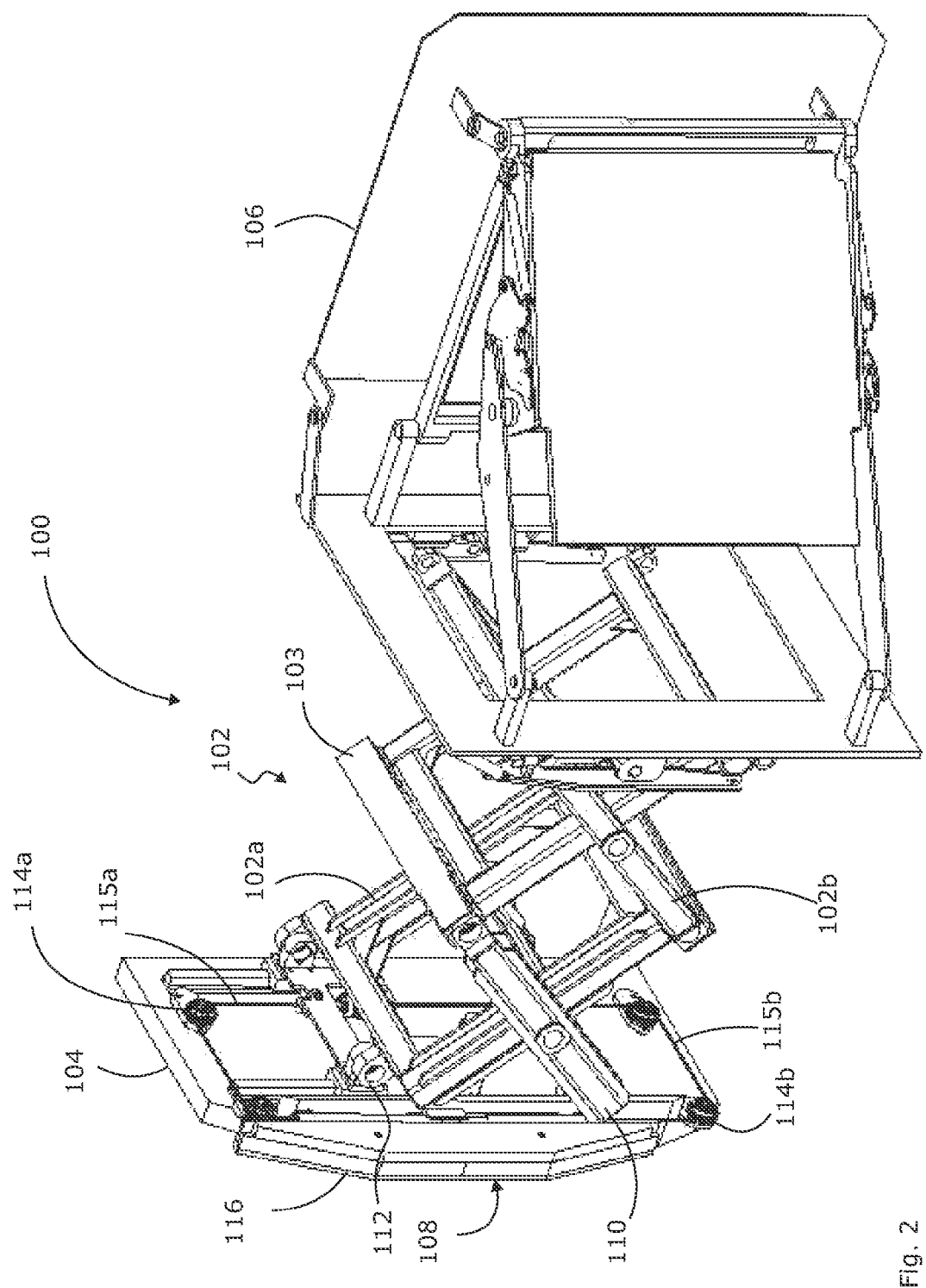
FIG. 2 is a perspective view of an extendible support mechanism according to embodiments of the present invention.
Figure 3:
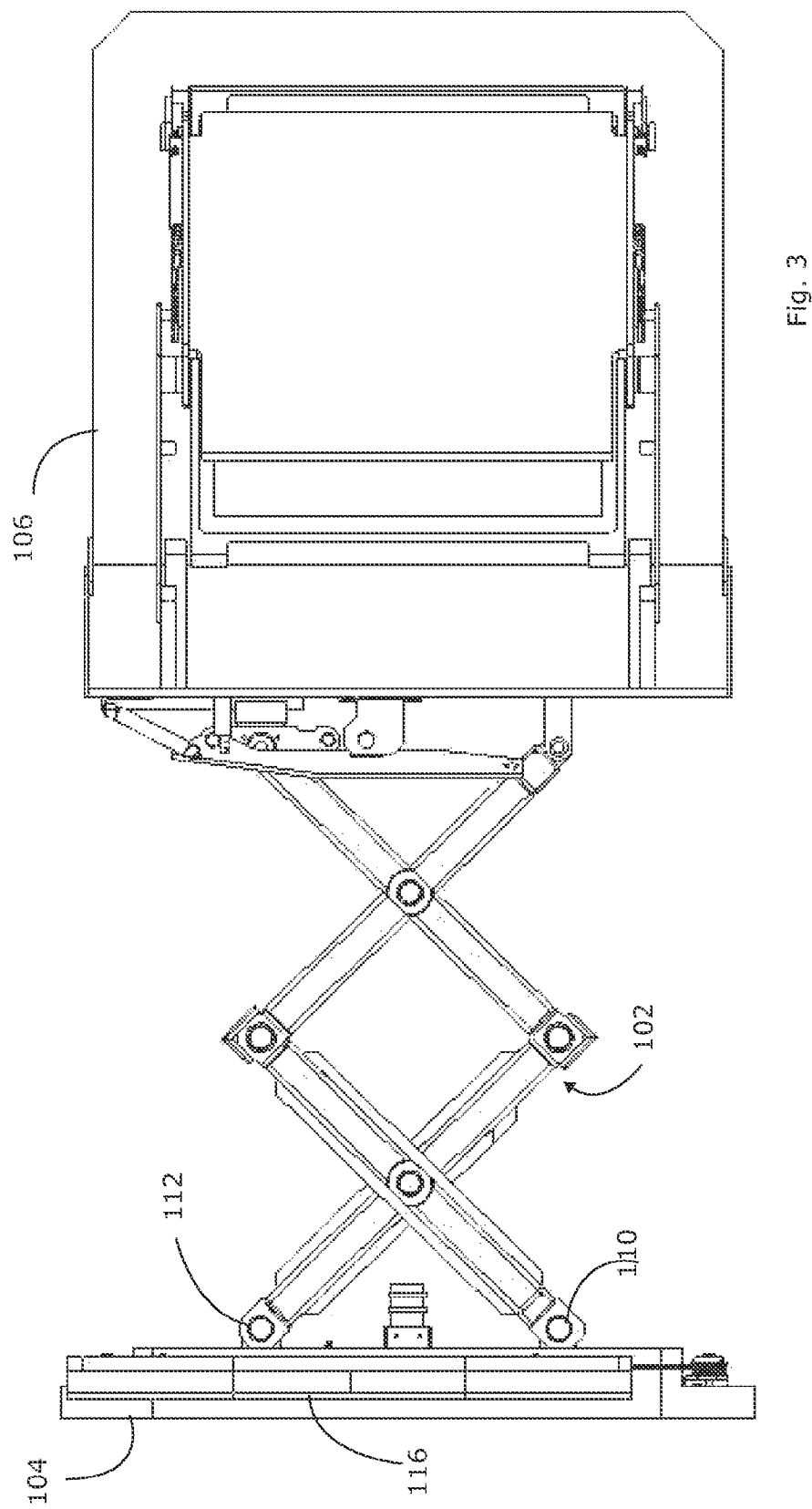
FIG. 3 is a side-on view of an extendible support mechanism according to embodiments of the present invention in its extended position.

FIGS. 2 and 3 show an extendible support mechanism 100 according to embodiments of the present invention in its extended position.

The mechanism comprises a scissors-type extending arm 102, i.e. two members are pivotally linked to one another at their centres to form a pair of members, and a plurality of such pairs are linked to each other by pivotal connection at their respective ends. By opening or closing one pair of interconnected members, each pair in the arm is also opened or closed, resulting in extension or retraction of the arm as a whole. In the illustrated embodiment, two parallel extending arms 102a, 102b are linked together by cross-members 103 to give the support structure as a whole the necessary rigidity.

The extending arm 102 is coupled at one end to a mount 104, suitable for attachment to a wall or any other mounting point. As will be seen in reference to FIG. 5, the mount 104 may be affixed to the rotatable gantry of a radiotherapy system. At the other end the arm 102 is coupled to the device to be supported, in the illustrated embodiment an imaging device 106 and specifically a portal imaging device.

The arm 102 is coupled to the mount 104 via the ends 110, 112 of the pair of members closest to the mount. As will be apparent from the description above, in extending and retracting the arm 102 these two ends will move relative to each other. Therefore some provision needs to be made for this. Both contacts points 110, 112 are allowed to pivot. One of the contact points 112 is allowed to slide, while the position of the other contact point 110 is fixed. In this way, both contact points 110, 112 can maintain contact with the mount 104, while also allowing the extension arm 102 to extend and retract. Of course, some driving means (not illustrated) is necessary to drive the extension and retraction of the arm 102, for example by driving the sliding contact point 112. The driving means may be provided with the device (for example a motor), or by the user of the device (i.e. manually driven).

However, as noted above, such a connection mechanism means that the centre of gravity of the arm varies as the extension arm 102 is retracted and extended. For example, first assume that the arm shown in FIG. 3 is oriented such that gravity acts vertically down the page. In this orientation, extension of the arm results in the contact point 112 sliding downwards and a drop in the centre of gravity; effectively, the action of gravity is to urge the arm to extend. Conversely, contraction of the arm results in the contact point 112 sliding upwards; in order to contract the arm, its weight must be lifted placing a strain on the driving means and the contact points. This problem is exacerbated when the extension arm 102 is mounted to a rotatable object, such as the gantry of a radiotherapy system. In that case, the arm shown in FIG. 3 may at some times be oriented with gravity acting vertically down the page (as described above), and at other times oriented with gravity acting vertically up the page. In the latter orientation, the effect of gravity is to urge the extension arm to retract, not extend.

According to embodiments of the present invention, this problem is solved by the provision of a counterbalancing system 108. In the illustrated embodiment (see again FIGS. 2 and 3), the counterbalancing system comprises a counterweight 116 coupled to the sliding contact point 112 via respective pulleys 114a, 114b and respective lines 115a, 115b. The contact point 112 is able to slide in two directions, which we shall term "up" and "down" for ease of reference (although as noted above the mount may be oriented in any direction with respect to gravity). A first set of pulleys 114a and a first line 115a connects the contact point 112 to the counterweight 116 as from the "upwards" direction. Thus, in an orientation where gravity acts vertically down the page in FIG. 3, the pulleys 114a and the line 115a are sufficient to counterbalance the act of gravity on the arm 102. If the mount 104 is not rotatable (or fixed to an object which is itself rotatable), these features alone are sufficient.

If the mount is rotatable or fixed to a rotatable object, a second set of pulleys 114b and a second line 115b connects the sliding contact point 112 as from the "downwards" direction (it will be apparent to those skilled in the art that the two lines 115a, 115b may in fact be a single continuous line appropriately connected to the counterweight 116). If gravity acts up the page in the orientation of FIG. 3, due to rotation of the arm, these features take over the counterbalancing function. Thus, the arm 102 is counterbalanced in substantially any orientation, and specifically in any angle of rotation.

Figure 4:
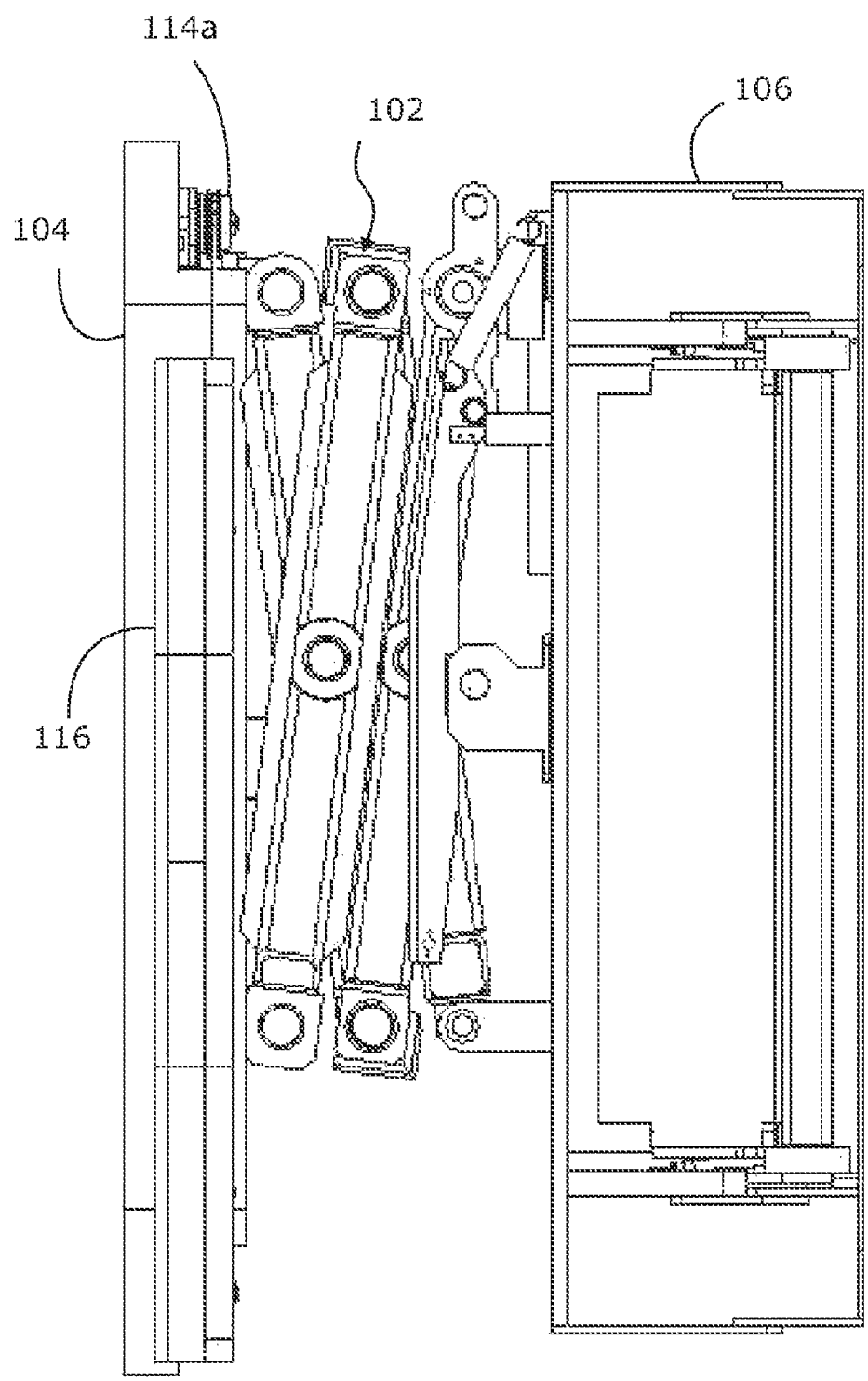
FIG. 4 is a side-on view of an extendible support mechanism according to embodiments of the present invention in its retracted position.

FIG. 4 shows the apparatus in its retracted position. The sliding contact point 112 has moved up the page as the arm 102 retracts. The counterweight 116 has moved down the page, such that overall the centre of gravity remains at the same height.

Figure 5:
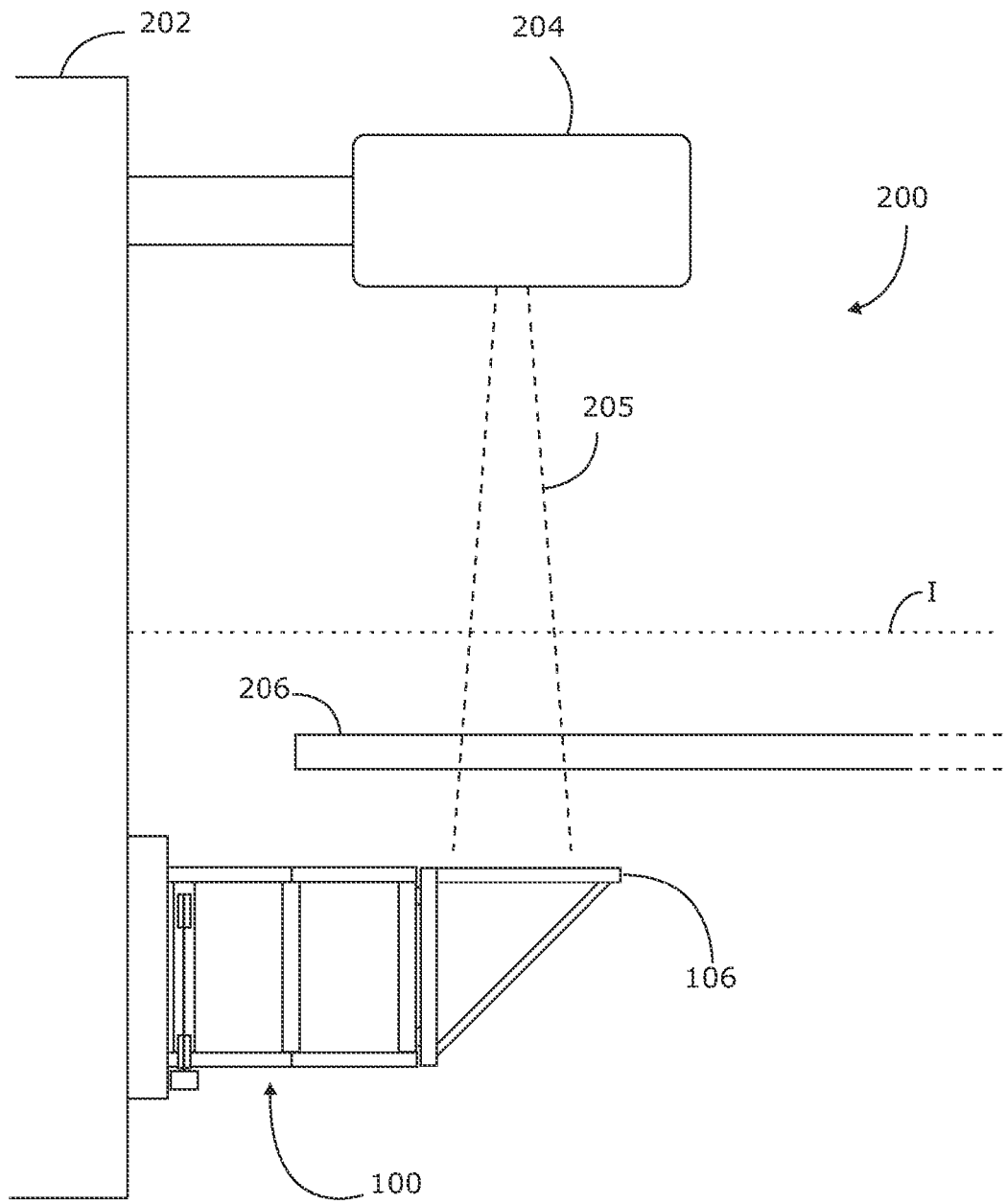
FIG. 5 shows a radiotherapy system according to embodiments of the present invention.

FIG. 5 shows an application of the extendible support apparatus 100 according to embodiments of the present invention in a radiotherapy system 200. The radiotherapy system 200 comprises a gantry 202, which can rotate about an axis I. A source of radiation (such as a linear accelerator) 204 is mounted on the gantry and directs a beam of radiation 205 towards a patient on a support 206. Generally, the support 206 is positioned such that a target region within the patient lies on the axis I, and the beam of radiation 205 is directed to intersect the axis I (also known as the isocentre); however, some treatment plans will allow the radiation to be directed away from the axis. A portal imaging device 106 is also mounted on the gantry 202 via a support mechanism 100 according to embodiments of the invention.

During treatment, the gantry 202 will rotate about the axis I, such that radiation can be directed towards the target region within the patient from a plurality of different angles (reducing the negative impact of the radiation on surrounding healthy tissue). The portal imager 106 may or may not be needed at these angles, and where not needed it is better for it to be stored out of the line of the radiation beam. The mechanism 100 is such that extension and retraction of the portal imager 106 requires the same amount of mechanical effort whatever the angle of rotation of the gantry.

The present invention thus provides an extendible support mechanism in which a counterbalance system allows extension and retraction of the arm to be carried out with the same level of mechanical effort. Embodiments of the present invention allow the system to be used in a plurality of orientations, and thus the invention has particular utility in the extension and retraction of peripheral devices for radiotherapy systems, where use of a rotatable gantry is common.

It will of course be understood that many variations may be made to the above-described embodiment without departing from the scope of the present invention.

The invention claimed is:

1. An apparatus for supporting a device, comprising:
   a mount;
   a scissors-type extension arm comprising, at a first end, a first contact point positionally fixed but pivotally connected to the mount and a second contact point pivotally and slidably connected to the mount, and, at a second end, an interface for connection to the device; and
   a counterbalancing system having a counterweight coupled to the second contact point of the scissors-type extension arm and arranged to counterbalance the scissors-type extension arm and the device in a plurality of spatial orientations of the apparatus.

2. The apparatus according to claim 1, wherein the second contact point is slidable in two, opposing directions, corresponding to extension and retraction of the scissors type extension arm, and wherein the counterbalancing system is arranged to counterbalance movement of the second contact point in either direction.

3. The apparatus according to claim 1, wherein the counterweight is coupled to the second contact point as from a plurality of directions.

4. The apparatus according to claim 1, wherein the device is a portal imager for a radiotherapy system.

5. An imaging apparatus for a radiotherapy system, comprising:
   a mount, for fixing to the radiotherapy system;
   an imaging device;
   an arm coupling the imaging device to the mount, the arm and imaging device having a combined centre of gravity, the arm being capable of extension, resulting in movement of the centre of gravity in a first direction, and retraction, resulting in movement of the centre of gravity in a second, opposite direction; and
   a counterweight, coupled to the arm so as to move in a direction opposing the movement of the centre of gravity when the arm is extended or retracted.

6. The imaging apparatus of claim 5, wherein the arm is a scissor-type extension arm.

7. The imaging apparatus of claim 5, wherein the arm comprises a pair of cross-members pivotally linked to each other at their respective mid-points.

8. The imaging apparatus according to claim 7, wherein the arm comprises at least one further pair of cross-members pivotally linked to each other at their respective mid-points, the at least one further pair being pivotally coupled to the pair of cross members at their respective ends.

9. The imaging apparatus according to claim 5, wherein the imaging apparatus is a portal imaging apparatus.

10. A peripheral apparatus for a radiotherapy system, comprising:
    a mount, for fixing to the radiotherapy system;
    a peripheral device;
    an arm coupling the peripheral device to the mount, the arm and peripheral device having a combined centre of gravity, the arm being capable of extension, resulting in movement of the centre of gravity in a first direction, and retraction, resulting in movement of the centre of gravity in a second, opposite direction; and
    a counterweight, coupled to the arm so as to move in a direction opposing the movement of the centre of gravity when the arm is extended or retracted.

* * * * *